June 19, 1956 L. L. BROOKS Plant Pat. 1,484

AZALEA PLANT

Filed May 6, 1955

Inventor
LENARD L. BROOKS
BY Clarence A. O'Brien
and Harvey B. Jacobson
Attorneys United States Patent Office Plant Pat. 1,484

Patented June 19, 1956

1,484

AZALEA PLANT

Lenard L. Brooks, Modesto, Calif.

Application May 6, 1955, Serial No. 506,686

1 Claim. (Cl. 47—60)

This invention is directed to a new and distinct variety of azalea plant, such plant being characterized by its beautiful orange red hose in hose flowers, its ease of reproduction on its own roots, its beautiful deep green foliage, and its high value as a greenhouse forcing or garden variety.

The instant variety is a cross produced in the experimental garden of my nursery at Modesto, California; the cross being made by pollen from the Kurume azalea Hexe used on the Belgian Indica azalea Wm. Van Orange; neither of the parent varieties being patented.

The cross as produced was recognized by me as possessing novel characteristics and appeared suitable for commercial use. It was therefore taken for propagation by cuttings, and the first cuttings produced azalea plants which carried forward all the distinguishing features of the parent.

The original asexual reproduction of the variety by cuttings was carried out in my experimental garden at Modesto, California. Subsequent propagations of the variety by cuttings further evidence that the variety is fixed in its floricultural characteristics.

Referring now more specifically to the botanical details of the new and distinct variety of azalea plant, the following is an outline description of the same.

PLANT

Form: Many branched, rounded, symmetrical form. The height and breadth of the young plants are about the same, but as the plant ages the breadth gradually becomes greater.

Growing habit: Dense and bushy with heavy dark green foliage. The rate of growth is quite similar to the Indica azaleas, but this variety produces many more branches and, therefore, many more flowers.

Blooming habit: It blooms out evenly over the entire plant when it is forced in the greenhouse or naturally flowered in the garden. It produces usually two flowers, or more, on each stem.

Blooming season: March-April in central California. It is very easily forced into flower out of season in the greenhouse.

Foliage:

*Size.*—The maximum size of the matured leaf is 1 inch wide and 2 inches long. Each plant will have many smaller leaves. The size of the leaves is determined principally by the feeding program.

*Color.*—On outdoor grown plants the color is about Brewster green. Underside is a lighter green. The color of the azalea foliage will vary widely, depending on the pH value and other factors in the soil. The present color determinations were made on plants properly fed and growing under correct pH values.

*Shape.*—Broad, ovate, pointed.

*Aspect.*—Glossy and nearly smooth.

*Texture.*—Medium.

*Edges.*—Minute hairs and serrations.

*Ribs and veins.*—Normal.

Flower:

*Size.*—Average 2½".

*Borne.*—Usually two on each stem, rarely more.

*Stem.*—Medium length, strong.

Figure 1:
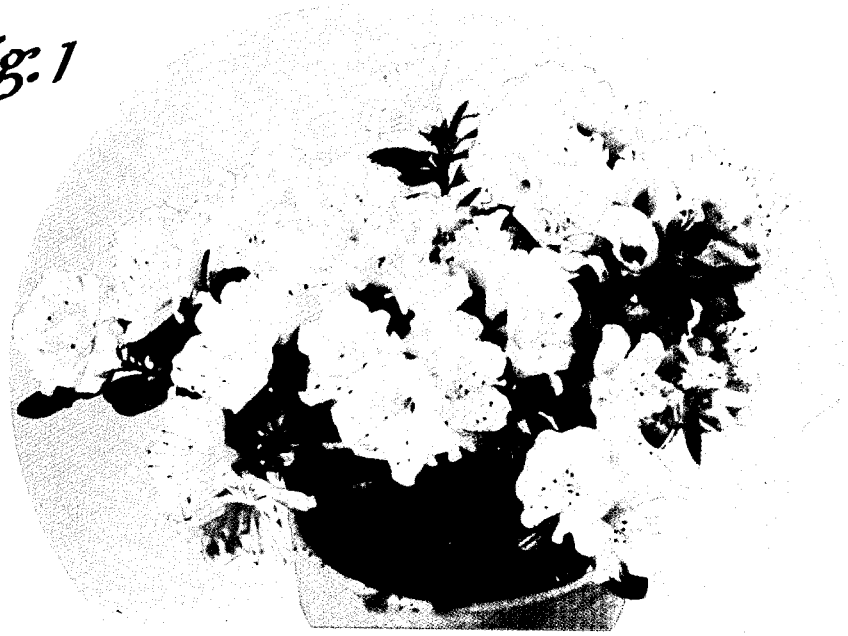
Fig. 1 is a perspective view showing the flowers in bloom.
Figure 2:
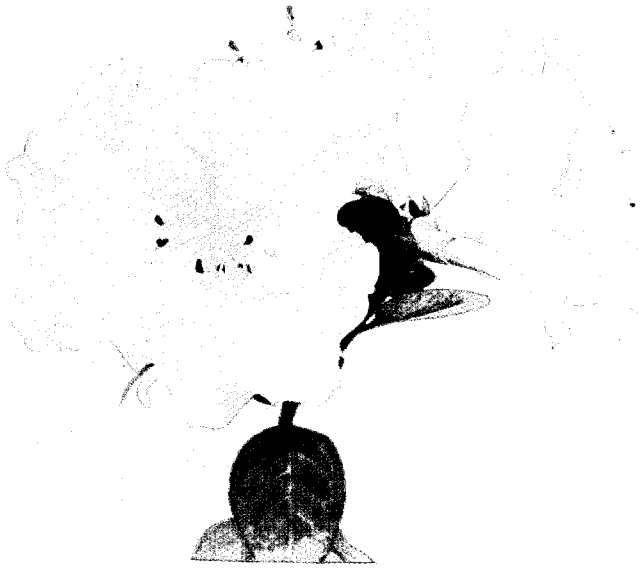
Fig. 2 is another perspective view of a stem, with leaves and flowers, showing the particular arrangement of the flower.

*Form.*—Hose in hose. Has a tendency to doubleness, as can be observed in the flower to the extreme left, Fig. 1. Petals are slightly ruffled.

*Permanence.*—Long lasting, with little or no fading or changing colors as the flowers age.

*Petalage.*—Five petals on each hose or flower after having antheferus petaloids in the center, which are in addition to the regular hose in hose flower.

*Color.*—Orange red.

Petals:

*Texture.*—Heavy.

*Appearance.*—Velvety, inside and out. Edges only slightly ruffled.

*Size.*—1¼" to 1½" long, ⅞" to 1⅛" wide.

*Shape.*—Ovate, pointed. Ruffled in such a manner as to give the illusion that it is much more pointed than it actually is.

*Arrangement.*—Normal Kurume type.

*Persistence.*—Remains firm without wilting or changing color until flower is ready to fall.

Reproductive organs:

*Stamens.*—Five. Anther blackish. Filament about same color as the flower.

*Pollen.*—White.

*Style.*—About the same color as petals. Stigma darker.

*Ovaries.*—Normal.

The color designations according to "A Dictionary of Color" by Maerz and Paul are as follows:

| Part | Color | Plate | Letter | Number |
|---|---|---|---|---|
| Foliage: | | | | |
| New Leaves | -------- | 23 | L | 3 to 6 |
| Mature leaves | -------- | 24 | L | 1 |
| Stems (new growth) | -------- | 16 | A | 12 |
| Flower: | | | | |
| Outer edges of petals | -------- | 3 | J | 6 |
| Base of petals | -------- | 4 | L | 10 |

As compared to other varieties of azalea plants, the present variety somewhat resembles Hexe, the pollen parent, but with the following principal differences:

1. The plant grows more compactly, producing more flowers.
2. The flowers are larger.
3. The color is much brighter and, having more orange and less blue, it shows up much better under all conditions, particularly under artificial light.

Tests indicate that this variety has approximately the hardiness of Hexe, and that it starts just as easily from cuttings.

Having thus described the invention, I claim:

A new and distinct variety of azalea plant substantially as shown and described, of the Kurume class, comprised of a cross between the Kurume azalea Hexe and the Belgian Indica azalea Wm. Van Orange, characterized particularly by its beautiful orange red hose in hose flowers, its ease of reproduction on its own roots, its much branched, compact habit of growth, its beautiful dark green foliage, and its high value as a greenhouse forcing or garden variety.

No references cited